United States Patent [19]

Mohamed

[11] Patent Number: 5,484,450
[45] Date of Patent: Jan. 16, 1996

[54] PENILE PROSTHESIS IMPLANT INSERTION INSTRUMENT

[76] Inventor: Adel W. Mohamed, P.O. Box 2266, Smithfield, N.C. 27577

[21] Appl. No.: 262,659

[22] Filed: Jun. 20, 1994

[51] Int. Cl.⁶ .................................................. A61B 19/00
[52] U.S. Cl. .............................................. 606/108; 600/40
[58] Field of Search .............................. 606/1, 159, 222, 606/106–108, 232, 190, 205–210; 30/325, 149, 346, 121, 113.1; 128/20; 142/56; 600/40

[56] References Cited

U.S. PATENT DOCUMENTS

| | | | |
|---|---|---|---|
| 470,676 | 3/1892 | Jackson | 30/149 |
| 5,056,223 | 10/1991 | Buck et al. | 30/113.1 |
| 5,281,230 | 1/1994 | Heidmueller | 606/205 |

FOREIGN PATENT DOCUMENTS 1126617  11/1956  France .

Primary Examiner—Stephen C. Pellegrino
Assistant Examiner—Glenn Dawson
Attorney, Agent, or Firm—Cushman Darby & Cushman

[57] ABSTRACT

An instrument for use in penile prosthesis implant surgery or similar operation, the implant including a pair of inflatable, generally cylindrical members made of silicone material and a fluid tube coupled to each cylindrical member. The instrument is constructed and arranged to prevent damage to a cylindrical member upon closing an incision by suturing, the incision being made for the purpose of inserting the cylindrical member into the corpus cavernosum of the penis or for accessing the cylindrical member within the penis. The instrument includes an elongated handle and an elongated tool extending from the handle. The tool includes a connecting portion connected to the handle and a distal tool portion extending from the connecting portion. The distal tool portion is in the form of an arcuate wall defining a smooth concave surface and a smooth convex surface opposite the concave surface. The arcuate wall includes surfaces defining a notch in a distal end which opens away from the handle.

8 Claims, 2 Drawing Sheets

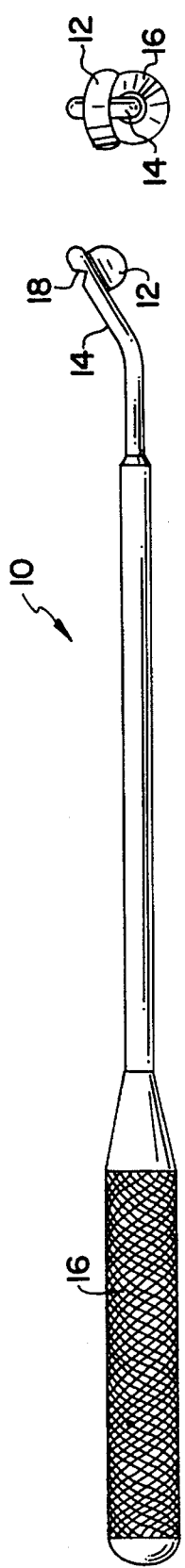
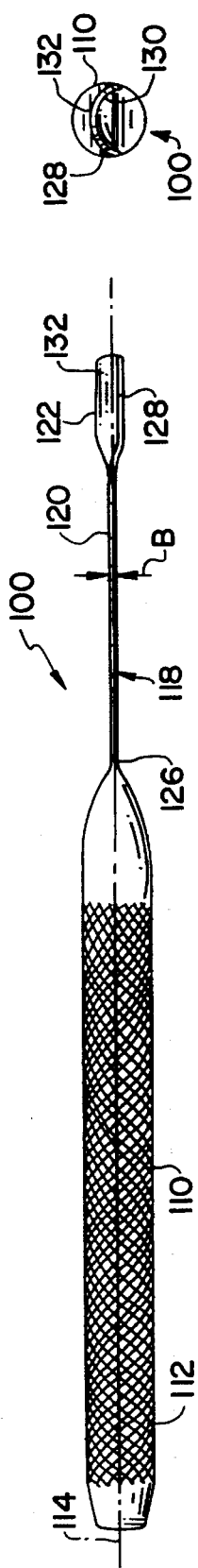
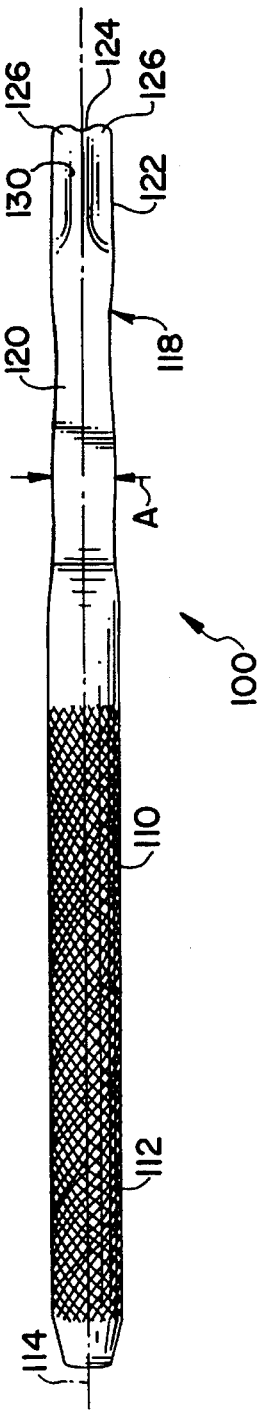
FIG. 1 (PRIOR ART)
FIG. 2 (PRIOR ART)
FIG. 3
FIG. 4
FIG. 5

PENILE PROSTHESIS IMPLANT INSERTION INSTRUMENT

BACKGROUND OF THE INVENTION

This invention relates to a closing instrument utilized in penile prosthesis implant surgery and, more particularly, to an instrument for assisting in closing an incision in the penis after insertion of an inflatable penile prosthesis therein.

Penile prosthesis products have been developed for use in treatment of chronic, organic male erectile dysfunction (impotence) in men who are suitable candidates for implantation surgery. Currently, there are several different penile prosthesis units that can be utilized. An example is the AMS 700™ inflatable penile prosthesis manufactured by American Medical Systems, Inc. The prosthesis includes two generally cylindrical members or cylinders which are inflatable. The size of the inflatable cylinders are chosen to be of the size which will fit within the corpus cavernosum of the patient. The cylinders are typically made of solid silicone, are very soft, and capable of being inflated by a fluid preferably liquid. Each cylinder has a fluid tube connected thereto between the ends at a position spaced further from the distal end and closer to the proximal end thereof. A pump is disposed in the scrotum, and an abdominal reservoir is provided. The cylinders are inflated as fluid is pumped from the reservoir, and are deflated as fluid is transferred back to the reservoir. This inflation and deflation allows the patient to control whether his penis is erect or flaccid.

During the surgical operation of inserting the cylinders, an incision is made in each corpus cavernosum in a position which corresponds generally to the position of the fluid tube. The portion of the cylinder forwardly of the fluid tube is fed into the corpus cavernosum through the incision and is pulled forwardly into the major portion of the corpus cavernosum which extends forwardly of the incision. When the forward portion has reached its proper position, the tube is bent at the position adjacent the fluid tube and the rear end is then inserted into the rearward portion of the corpus cavernosum, completing the insertion of the cylinder. The process is repeated for the other cylinder.

Instruments have been developed to assist in closing an incision made for the purpose of inserting the prosthesis. An example of such an instrument is shown in FIG. 1. The instrument 10 includes a very short arcuate spoon-like element 12 welded on its convex side to a rigid, rod-shaped element 14. The rod-shaped element 14 extends rearwardly from the spoon-like element 12 and is formed with an angular turn. Element 14 is connected to the instrument handle 16. The distal end of the rod-shaped element 14, which is welded to the spoon-like element 12 has a V-shaped notch 18 formed in the exterior thereof. The notch 18 enables a suture needle (not shown) to extend therethrough during a suturing operation to close the incision.

The instrument 10 has been found difficult to use since it is difficult to coordinate or align the V-shaped notch with the suture needle during the incision closing procedure. Consequently, there exits a need to provide an implant incision closing instrument which is more convenient to use and otherwise overcomes the disadvantages of the instruments of the prior art.

SUMMARY OF THE INVENTION

An object of the present invention is to fulfill the need expressed above. The present invention is based upon the underlying concept that the improved incision closing instrument herein disclosed will not only fulfill the need above, but can be used to perform other functions as well, as assisting in the insertion of the prosthesis into the penis. In accordance with the principles of the present invention, this objective is achieved by utilizing the above expressed underlying concept by providing an instrument for use in penile prosthesis implant surgery wherein the implant comprises a pair of inflatable, generally cylindrical members made of silicone material and capable of being easily punctured by a needle point, and a fluid tube coupled to each cylindrical member. The instrument is constructed and arranged to aid in the final insertion of each cylindrical member into the corpus cavernosum of the penis and to prevent damage to each implanted cylindrical member upon closing an incision by suturing. The instrument includes an elongated handle constructed and arranged to be grasped and maneuvered by a user, and an elongated tool extending from the handle. The tool includes a connecting portion connected to the handle and a distal tool portion extending from the connecting portion. The distal tool portion is in the form of an arcuate wall portion defining a smooth concave surface and a smooth convex surface opposite the concave surface. The arcuate wall portion has surfaces defining a notch in a distal end which opens in a direction away from the handle and divides the distal end into two spaced, side-by-side lobe-like sections. The surfaces defining the notch are constructed and arranged to engage the air tube of an associated cylindrical member so as to move a portion of the cylindrical member into a portion of the corpus cavernosum of the penis. The concave surface is constructed and arranged to conform to an external shape of each cylindrical member, such that movement of the distal end into the incision so that the concave surface is disposed about a portion of a cylindrical member protects the cylindrical member portion from inadvertent puncture by a suture needle during closing of the incision.

A further object of the present invention is the provision of a closing instrument of the type described which is simple in construction, effective in operation and economical to manufacture.

These and other objects of the present invention will become more apparent during the course of the following detailed description and appended claims.

The invention may best be understood with reference to the accompanying drawings wherein an illustrative embodiment is shown.

BRIEF DESCRIPTION OF THE DRAWINGS

FIG. 1 is a side elevational view of a conventional closing instrument for use in penile prosthesis implant surgery;

FIG. 2 is an end view of the conventional instrument of FIG. 1;

FIG. 3 is a side elevational view of a closing instrument for use in penile prosthesis implant surgery, embodying the principles of the present invention;

FIG. 4 is a end view of the closing instrument of FIG. 3;

FIG. 5 is a plan view of the closing instrument of FIG. 3; and

DETAILED DESCRIPTION OF THE PRESENTLY PREFERRED EXEMPLARY EMBODIMENT

Figure 6:
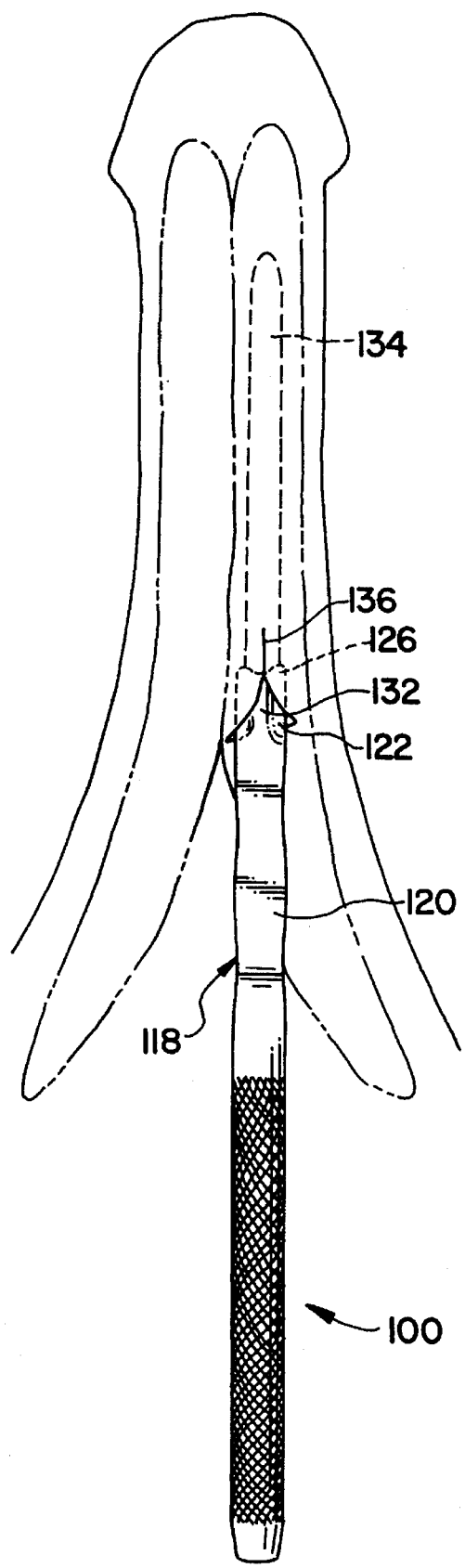
FIG. 6 is a schematic illustration of the instrument of FIG. 3 being used to close an incision in a penis made for the purpose of inserting a penile prosthesis therein.

Referring now more particularly to the drawings, there is shown in FIGS. 3–5 thereof a closing instrument, preferably for use in penile implant surgery, generally indicated at 100, which embodies the principles of the present invention. The instrument 100 includes an elongated handle 110 which includes a knurled, grip portion 112 extending longitudinally along axis 114 thereof so as to be gripped and maneuvered by a user. In the illustrated embodiment, the handle 110 is in the form of a hollow elongated cylinder having a diameter of approximately 10 mm. It can be appreciated that the handle 110 can be configured in any convenient shape suitable for gripping. As shown, the handle 110 gradually tapers, as viewed from the side (FIG. 3), and joins with an elongated tool 118. The tool 118 extends longitudinally from the handle 110. The length of the tool 118 is approximately 60 mm and the overall length of the instrument 100 is approximately 180 mm.

In the illustrated embodiment, the tool 118 includes a connecting portion 120 connected to the handle 110. As shown in FIGS. 3 and 5, the connecting portion 120 is generally planar, having a maximum width A of approximately 8 mm, and a minimal cross-sectional thickness B approximately 1 mm, which is substantially less than the cross-sectional thickness of the handle 110. It can be appreciated, however, that the connecting portion 120 need not be planar, but can be of any configuration, for example, cylindrical, that can be bent easily with respect to the handle 110.

The tool 118 includes a distal tool portion 122 extending longitudinally from the connecting portion 120. The distal tool portion is in the form of an arcuate wall 128, defining a smooth concave surface 130, constructed and arranged to define a recess of generally constant depth, as shown in FIG. 4, so as to be complimentary to the external shape of a cylindrical member of the prosthesis, and a smooth convex surface 132, opposite the concave surface 130. The arcuate wall 128 has a surfaces defining a notch in a distal end which opens in a direction away from the handle 110 and divides the distal end into two spaced, side-by-side lobe-like sections 126. The surfaces defining the notch are constructed and arranged to engage the air tube associated with each cylindrical member so as to move a portion of the cylindrical member into a portion of the corpus cavernosum of the penis, as will be explained below.

The instrument 100 is preferably made of stainless steel or other material typically used for surgical procedures.

The use of the closing instrument 100 during a surgical operation for inserting a penile prosthesis will be appreciated below with reference to FIG. 6. As noted above, in the surgical operation, an incision is made in each corpus cavernosum corresponding generally to the position of the fluid tube of the prosthesis. The closing instrument 100 is first used in the procedure to aid in moving the rearward portion of each cylindrical member 134 into the rearward portion of the corpus cavernosum which receives the same. The notch 124 of the instrument 100 is adapted to be positioned on the fluid tube at its juncture with the cylinder 134. The attending surgeon simply uses the instrument 100 to push against the fluid tube to move the rear portion of the cylindrical member 134 into the corpus cavernosum.

After each cylindrical member 134 is mounted within the corpus cavernosum, it becomes necessary to close the incision 136 which was made to effect the insertion of the cylindrical members 134. This closing is accomplished by a conventional curved needle and a suture material (not shown). The closing instrument 100 provides a means to prevent the needle point from puncturing the wall of the cylindrical member 134 as the sutures are made to close the incision. The distal tool portion 122, including the arcuate wall 128, is inserted through the incision 136 so that the concave surface 130 thereof engages the exterior surface of the cylindrical member 134 in the area where the needle is being inserted (FIG. 6). As each suture is made, the suture needle may contact the smooth the convex surface 132 of the arcuate wall 128, without damaging the portion of the cylindrical member which is covered by the concave surface 130. Thus, during the suturing procedure, the surgeon need not align the suture needle with a notch in the tool as is required in the conventional device of FIG. 1. As each suture is made, the instrument 100 is withdrawn until there are two final sutures to be made. In making these sutures, it is most preferable to keep the final sutures in a loose condition and then withdraw the instrument from the incision. Thereafter, the sutures are tightened to finally close the incision. Alternatively, in making the final two sutures, the instrument 100 may be turned so that the notch 124 is extending into the incision 136 permitting one of the lobe-like structures 126 to cover a portion of the cylindrical member 134, thereby preventing damage thereto. This type of procedure may be used in the last two sutures which finally closes the incision 136.

The instrument 100 is used in inserting both cylindrical members 134. The thickness of the connecting portion 120 enables it to be bent manually with respect to the handle 110 so that the distal tool portion 122 may be selectively offset from the longitudinal axis 114 of the handle. Bending of the connecting portion 120 into different angular configurations may be desirable in manipulating the instrument 100, depending on the particular situation.

It has thus been seen that the closing instrument 100 of the present invention provides a tool which is easily manipulated for use during both insertion of a prosthesis and during closing of an incision made for insertion of the prosthesis, so as to protect the cylindrical member of the penile prosthesis during suturing. It can be appreciated, however, that the instrument 100 is not limited to use in penile prosthesis implant surgery. The instrument may be used in similar operations to protect other tubular members, for example, the ureter and urethra, upon closing an incision. It can be appreciated that the concave surface of the instrument may be sized and configured to accommodate the particular size of the tubular member to be protected.

It has thus been seen that the objects of this invention have been fully and effectively accomplished. It will be realized, however, that the foregoing preferred specific embodiment has been shown and described for the purpose of this invention and is subject to change without departure from such principals. Therefore, this invention includes all modifications encompassed within the spirit and scope of the following claims.

What is claimed is:

1. An instrument for use in penile prosthesis implant surgery, the implant being of the type including a pair of inflatable, generally cylindrical members made of silicone material and capable of being punctured by a needle point and a fluid tube coupled to each cylindrical member, the instrument being constructed and arranged to aid in the final insertion of each cylindrical member into a corpus cavernosum of the penis and prevent damage to a cylindrical member upon closing an associated incision by suturing, the incision being made for the purpose of inserting the cylindrical member into a corpus cavernosum of the penis or for accessing the cylindrical member within the penis, the instrument comprising:

an elongated handle constructed and arranged to be grasped and maneuvered by a user, and an elongated tool extending from said handle, said tool including a connecting portion connected to said handle and a distal tool portion extending from said connecting portion and sized for insertion into a corpus cavernosum of the penis, said distal tool portion being in the form of an arcuate wall defining a smooth concave surface and a smooth convex surface opposite said concave surface, said arcuate wall including surfaces defining a notch in a distal end which opens away from the handle, the surfaces defining the notch being constructed and arranged to engage the fluid tube of an associated cylindrical member so as to move a portion of the cylindrical member into a portion of the corpus cavernosum of the penis, said concave surface defining a recess of generally constant depth so as to be complimentary to an external shape of the cylindrical member, whereby movement of the distal tool portion into the incision so that the concave surface is disposed about a portion of the cylindrical member protects the cylindrical member portion from inadvertent puncture by a suture needle during closing of the incision.

2. The instrument according to claim 1, wherein said notch divides said distal end into two spaced, side-by-side lobe-like sections.

3. The instrument according to claim 1, wherein said connecting portion has a minimal cross-sectional thickness substantially less than a cross-sectional thickness of said handle and generally the same cross-sectional thickness of said distal tool portion permitting said connecting portion to be manually bent with respect to the handle enabling the distal tool portion to be selectively offset from a longitudinal axis of the handle.

4. The instrument according to claim 1, wherein said connecting portion is an elongated, generally planar portion having a minimal cross-sectional thickness of approximately 1.0 mm, said handle being generally cylindrical having a diameter of approximately 10 mm.

5. The instrument according to claim 1, wherein the handle and the tool are comprised of stainless steel.

6. The instrument according to claim 1, wherein the handle is in the form of a hollow cylinder.

7. A method of inserting a cylindrical member of a penile implant during penile prosthesis implant surgery with the use of an instrument, the implant being of the type including a pair of inflatable, generally cylindrical members made of silicone material and capable of being punctured by a needle point and an associated fluid tube coupled to each cylindrical member, the instrument comprising an elongated handle constructed and arranged to be grasped and maneuvered by a user, and an elongated tool extending from said handle, said tool including a connecting portion connected to said handle and a distal tool portion extending from said connecting portion and sized for insertion into a corpus cavernosum of the penis, said distal tool portion being in the form of an arcuate wall defining a smooth concave surface and a smooth convex surface opposite said concave surface, said arcuate wall including surfaces defining a notch in a distal end which opens away from the handle, said concave surface being constructed and arranged to be complimentary to an external surface of one of the cylindrical members, the method comprising:

making an incision in a corpus cavernosum;

moving a rearward portion of one cylindrical member of said pair of cylindrical members into a rearward portion of the corpus cavernosum so as to be in an initial position;

engaging the associated fluid tube coupled to said one cylindrical member with the notch of the instrument and pushing against the associated fluid tube with the instrument to move the rearward portion of said one cylindrical member into the corpus cavernosum so as to be in a final position;

inserting the distal tool portion through the incision so that the concave surface engages the external surface of said one cylindrical member in an area where a needle is to be used to close the incision;

closing a portion of the incision with sutures using a needle while ensuring that the convex surface of the distal tool portion is between said one cylindrical member and a point of the needle thereby preventing puncturing of said one cylindrical member; and removing the distal tool portion from the incision and thereafter ensuring that the incision is closed.

8. The method according to claim 7, wherein closing the incision includes keeping final sutures in a loose condition so that the distal tool portion may be removed from the incision, and after removing the distal tool portion from the incision, tightening the final sutures to ensure that the incision is closed.

* * * * *